United States Patent [19]
Christe et al.

[11] Patent Number: 5,369,212
[45] Date of Patent: Nov. 29, 1994

[54] METHOD OF PREPARING TETRAMETHYLAMMONIUM AZIDE

[75] Inventors: Karl O. Christe, Calabasas; William W. Wilson, Simi Valley, both of Calif.

[73] Assignee: The United States of America as represented by the Secretary of the Air Force, Washington, D.C.

[21] Appl. No.: 23,247

[22] Filed: Feb. 26, 1993

[51] Int. Cl.$^5$ .................. C07C 209/00; C07C 211/63
[52] U.S. Cl. ...................................... 564/296; 564/291
[58] Field of Search ..................... 552/5; 564/296, 291

[56] References Cited

U.S. PATENT DOCUMENTS

| | | | |
|---|---|---|---|
| 3,190,919 | 6/1965 | Swanson | 260/567.6 |
| 3,388,131 | 6/1968 | Urbau et al. | 260/290 |
| 4,092,466 | 5/1978 | Fletcher et al. | 526/13 |
| 4,216,168 | 8/1980 | Evans et al. | 260/567.6 M |
| 4,426,531 | 1/1984 | Bison et al. | 548/253 |

OTHER PUBLICATIONS

Journal of Organic Chemistry vol. 32, No. 9, pp. 2876–2880 Sep. 1967.

Christie, Karl O. et al, "New Synthesis, Crystal Structure and Vibrational Spectra of Tetramethylammonium Azide of the Fluoride Anion with HN$_3$ and of the Azide Anion with HF", J. American Chem. Soc., vol. 114, No. 9, 1992, pp. 3411–3414.

*Primary Examiner*—José G. Dees
*Assistant Examiner*—Samuel Barts
*Attorney, Agent, or Firm*—Donald J. Singer; Thomas C. Stover

[57] ABSTRACT

Tetramethylammonium azide, N(CH$_3$)$_4$N$_3$, is prepared by a new process per the present invention. In the prior art, preparation of such azide was by use of shock-sensitive starting materials, i.e. AgN$_3$ and HN$_3$. The method of the present invention provides a new method for making such azide at high purity, at room temperature, without the use of shock-sensitive materials.

3 Claims, No Drawings

METHOD OF PREPARING TETRAMETHYLAMMONIUM AZIDE

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to the preparation of tetramethylammonium azide, $N(CH_3)_4N_3$, particularly preparing such azide without using shock-sensitive material.

2. The Prior Art

Although tetramethylammonium azide, has been known since 1918, little information has been reported for this interesting compound. According to the previous reports, the compound was prepared by either the reaction of $N(CH_3)_4I$ with $AgN_3(1)$ in either water or anhydrous

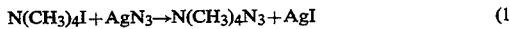

$$N(CH_3)_4I + AgN_3 \rightarrow N(CH_3)_4N_3 + AgI \quad (1)$$

ethanol or the neutralization of $N(CH_3)_4OH$ with aqueous $HN_3(2)$. Both preparations involve the use of shock-sensitive

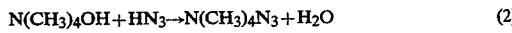

$$N(CH_3)_4OH + HN_3 \rightarrow N(CH_3)_4N_3 + H_2O \quad (2)$$

starting materials, i.e. $AgN_3$ and $HN_3$, and suffer from solubility and purification problems.

Accordingly, there is a need and market for preparation the above azide that overcomes the above prior art shortcomings.

There has now been discovered a method for preparation of such azide which avoids shock-sensitive starting materials and the high costs and light sensitivity of employing a silver salt per the above prior art method. Further the purity of the resulting azide, $N(CH_3)_4N_3$ is high.

SUMMARY OF THE INVENTION

Broadly the present invention provides a method for preparing $N(CH_3)_4N_3$ comprising, reacting the following:

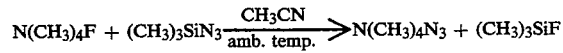

$$N(CH_3)_4F + (CH_3)_3SiN_3 \xrightarrow[\text{amb. temp.}]{CH_3CN} N(CH_3)_4N_3 + (CH_3)_3SiF$$

DESCRIPTION OF PREFERRED EMBODIMENT

The invention will become more apparent from the following detailed specification given below.

The problems of the previous synthesis of $N(CH_3)_4N_3$ were overcome by reacting $N(CH_3)_4F$ with commercially available $(CH_3)_3SiN_3$ at room temperature in $CH_3CN$ solution according to:

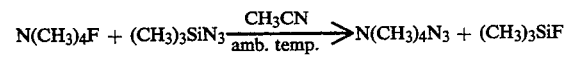

$$N(CH_3)_4F + (CH_3)_3SiN_3 \xrightarrow[\text{amb. temp.}]{CH_3CN} N(CH_3)_4N_3 + (CH_3)_3SiF$$

The conversion of $N(CH_3)_4F$ to $N(CH_3)_4N_3$ is quantitative, and since both trimethylsilyl compounds are volatile at room temperature, very pure and anhydrous $N(CH_3)_4N_3$ can be prepared by use of a slight excess of $(CH_3)_3SiN_3$ and removal of the solvent, $(CH_3)_3SiF$ and unreacted $(CH_3)_3SiN_3$ at room temperature. None of the materials used in the improved process are shock-sensitive and the high cost and light sensitivity of a silver salt are avoided. Furthermore, prolonged heating for $H_2O$ removal and subsequent extractions with $CH_3CN$ are not required, and the purity of the $N(CH_3)_4N_3$ prepared by the new process is excellent. The resulting azide compound is a white, crystallinic, nonsensitive and slightly hygroscopic solid. It has little solubility in cold $CH_3CN$, moderate solubility in hot $CH_3CN$ and is slightly soluble in alcohol and water.

For further discussion of prior art problems in preparing tetramethylammonium azide as well as of the safe preparation of such azide per the method of the present invention, see the following Article. The Article is published in the Journal of the American Chemical Society, 1992, Vol. 114, No. 9, pp. 3411–3414 and is entitled "New Synthesis, Crystal Structure, and Vibrational Spectra of Tetramethylammonium Azide and Reactions of the Fluoride Anion with $HN_3$ and of the Azide Anion with HF" by Karl O. Christe et al., which Article is incorporated herein by reference. Such Article provides considerable disclosure relative to the molecular structure of $N(CH_3)_4N_3$, its crystal structure, its vibrational spectra, certain related reactions as indicated by the above title of the Article, other physical properties of the above azide and other related data and numerous footnotes thereto, all incorporated herein by reference.

The following example is given in illustration of the method of the present invention and should not be construed in limitation thereof.

EXAMPLE I

Synthesis of $N(CH_3)_4N_3$. A solution of $Si(CH_3)_3N_3$ (29.92 mmol) in 15 mL of $CH_3CN$ was slowly added in a dry atmosphere to $N(CH_3)_4F$ (24.10 mmol) dissolved in 29 mL of $CH_3CN$. In a mildly exothermic reaction, a white precipitate was formed instantaneously. The mixture was agitated for about 10 min. and then all volatile material was pumped off at room temperature. The white solid residue (2.794 g; weight calculated for 24.10 mmol of $N(CH_3)_4N_3 = 2.797$ g, corresponding to a 99.9% yield) was identified by vibrational spectroscopy and a crystal structure determination, as $N(CH_3)_4N_3$. Its decomposition point was found to be 255° C. Further information as to the above properties is given in the above Article, incorporated herein by reference.

What is claimed is:

1. A method for preparing $N(CH_3)_4N_3$ comprising, reacting the following:

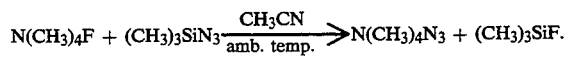

$$N(CH_3)_4F + (CH_3)_3SiN_3 \xrightarrow[\text{amb. temp.}]{CH_3CN} N(CH_3)_4N_3 + (CH_3)_3SiF.$$

2. The method of claim 1 employing a slight excess of $(CH_3)_3SiN_3$ to precipitate said $N(CH_3)_4N_3$ with subsequent removal of the volatiles, $(CH_3)_3SiF$ and unreacted $(CH_3)_3SiN_3$.

3. The method of claim 2 wherein 29.92 mmol of $Si(CH_3)_3N_3$ in 15 mL of $CH_3CN$ are slowly added to 24.10 mmol of $N(CH_3)_4F$ dissolved in 29 mL of $CH_3CN$ to yield 24.10 mmol of $N(CH_3)_4N_3$, with subsequent removal of said volatiles.

* * * * *